(12) United States Patent
Mirza et al.

(10) Patent No.: US 8,821,383 B2
(45) Date of Patent: Sep. 2, 2014

(54) SLOTTED CLEAR CANNULA

(75) Inventors: Ather Mirza, Smithtown, NY (US); Romi Mirza, Smithtown, NY (US)

(73) Assignee: A.M. Surgical, Inc., Smithtown, NY (US)

(*) Notice: Subject to any disclaimer, the term of this patent is extended or adjusted under 35 U.S.C. 154(b) by 1022 days.

(21) Appl. No.: 12/400,485

(22) Filed: Mar. 9, 2009

(65) Prior Publication Data

US 2010/0228083 A1 Sep. 9, 2010

(51) Int. Cl.
| | | |
|---|---|---|
| *A61B 1/04* | (2006.01) | |
| *A61B 1/018* | (2006.01) | |
| *A61B 17/32* | (2006.01) | |
| *A61B 1/317* | (2006.01) | |
| *A61B 1/00* | (2006.01) | |
| *A61B 17/00* | (2006.01) | |
| *A61B 1/313* | (2006.01) | |
| *A61B 17/34* | (2006.01) | |

(52) U.S. Cl.
CPC ............. *A61B 1/317* (2013.01); *A61B 1/018* (2013.01); *A61B 2017/00902* (2013.01); *A61B 17/320036* (2013.01); *A61B 1/313* (2013.01); *A61B 2017/00526* (2013.01); *A61B 1/00135* (2013.01); *A61B 17/3417* (2013.01)
USPC ............... 600/114; 600/121; 600/190

(58) Field of Classification Search
USPC ........... 600/114, 120, 190–200; 606/167–203
See application file for complete search history.

(56) References Cited

U.S. PATENT DOCUMENTS

| | | | | |
|---|---|---|---|---|
| 3,537,451 | A * | 11/1970 | Beck et al. | 604/165.03 |
| 3,885,560 | A * | 5/1975 | Baldwin | 604/177 |
| 4,246,897 | A * | 1/1981 | Muto | 128/207.15 |
| 4,324,236 | A * | 4/1982 | Gordon et al. | 604/272 |
| 4,364,391 | A * | 12/1982 | Toye | 128/207.29 |
| 4,596,559 | A * | 6/1986 | Fleischhacker | 604/164.05 |
| 4,683,879 | A * | 8/1987 | Williams | 128/200.26 |
| 5,098,392 | A * | 3/1992 | Fleischhacker et al. | 604/164.05 |
| 5,141,497 | A * | 8/1992 | Erskine | 604/164.05 |
| 5,167,634 | A * | 12/1992 | Corrigan et al. | 604/160 |
| 5,197,971 | A * | 3/1993 | Bonutti | 606/192 |
| 5,217,005 | A * | 6/1993 | Weinstein | 128/200.26 |
| 5,273,024 | A * | 12/1993 | Menon et al. | 600/114 |
| 5,282,816 | A * | 2/1994 | Miller et al. | 606/167 |
| 5,295,974 | A | 3/1994 | O'Laughlin | |
| 5,323,765 | A * | 6/1994 | Brown | 600/104 |
| 5,325,883 | A * | 7/1994 | Orr | 128/898 |
| 5,366,465 | A * | 11/1994 | Mirza | 606/170 |
| 5,489,273 | A * | 2/1996 | Whitney et al. | 604/160 |

(Continued)

OTHER PUBLICATIONS

Notification of Transmittal of the International Search Report and the Written Opinion of the International Searching Authority, Application No. PCT/US2010/026157, Form PCT/ISA/220 (Jul. 2010).

(Continued)

*Primary Examiner* — Matthew J Kasztejna

(74) *Attorney, Agent, or Firm* — Ping Wang; Andrews Kurth LLP

(57) ABSTRACT

A slotted cannula for endoscopic surgical procedures is disclosed. The slotted cannula has a tubular body having a distal end, a proximate end, an open slot extending longitudinally from the beginning of the proximate end to the proximity of the distal end, and a pair of wings integrally formed on the proximate end. The tubular body is made from a transparent material and has an inner diameter large enough to accommodate an endoscope.

31 Claims, 17 Drawing Sheets

(56) References Cited

U.S. PATENT DOCUMENTS

| | | | |
|---|---|---|---|
| 5,578,051 A | 11/1996 | Mirza | |
| 5,620,446 A * | 4/1997 | McNamara et al. | 606/79 |
| 5,649,946 A * | 7/1997 | Bramlet | 606/167 |
| 5,651,790 A * | 7/1997 | Resnick et al. | 606/167 |
| 5,665,093 A * | 9/1997 | Atkins et al. | 606/108 |
| 5,720,763 A * | 2/1998 | Tovey | 606/198 |
| 5,730,749 A * | 3/1998 | Battenfield | 606/167 |
| 5,743,882 A * | 4/1998 | Luther | 604/164.05 |
| 5,827,312 A * | 10/1998 | Brown et al. | 606/167 |
| 5,840,013 A * | 11/1998 | Lee et al. | 600/114 |
| 5,879,334 A * | 3/1999 | Brimhall | 604/165.04 |
| 5,908,431 A * | 6/1999 | Battenfield | 606/167 |
| 5,910,105 A * | 6/1999 | Swain et al. | 600/131 |
| 5,968,061 A * | 10/1999 | Mirza | 606/170 |
| 6,139,532 A * | 10/2000 | Howell et al. | 604/165.03 |
| 6,283,948 B1 * | 9/2001 | McKernan et al. | 604/272 |
| 6,402,677 B1 * | 6/2002 | Jacobs | 600/7 |
| 6,613,065 B2 * | 9/2003 | Lajtai | 606/190 |
| 7,041,115 B2 * | 5/2006 | Mirza et al. | 606/170 |
| 7,534,250 B2 * | 5/2009 | Schaeffer et al. | 606/191 |
| 7,780,690 B2 * | 8/2010 | Rehnke | 606/170 |
| 8,252,011 B1 * | 8/2012 | Forrester et al. | 606/167 |
| 2002/0019611 A1 | 2/2002 | Green | |
| 2002/0123724 A1 | 9/2002 | Douglas et al. | |
| 2005/0137528 A1 | 6/2005 | Wilkinson | |
| 2007/0270647 A1 * | 11/2007 | Nahen et al. | 600/131 |
| 2007/0288043 A1 * | 12/2007 | Rehnke | 606/170 |
| 2008/0045905 A1 * | 2/2008 | Chawki | 604/174 |
| 2008/0195128 A1 * | 8/2008 | Orbay et al. | 606/170 |
| 2008/0200758 A1 * | 8/2008 | Orbay et al. | 600/112 |

OTHER PUBLICATIONS

International Search Report and Written Opinion mailed Jun. 14, 2012 issued in International Patent Application No. PCT/US2011/064636.

* cited by examiner

SLOTTED CLEAR CANNULA

FIELD

The present invention relates to medical devices and, in particular, to a slotted cannula for endoscopic operations.

BACKGROUND

Endoscopic surgery is a minimally invasive surgical procedure that is performed through small incisions or natural body openings. An endoscopic procedure typically involves use of specialized devices and remote-control manipulation of instruments with indirect observation of the surgical field through an endoscope or similar device. Comparing to open surgery, endoscopic surgery may result in shorter hospital stays, or allow outpatient treatment.

Among more recent developments and advances in endoscopic surgical procedures, arthroscopic surgery employing the use of endoscopic devices has found widespread application. For example, endoscopic procedures have been successfully used in effectuating carpal tunnel release with specially designed endoscopic instruments, such as those described in U.S. Pat. No. 5,366,465, U.S. Pat. No. 5,578,051, U.S. Pat. No. 5,968,061, and U.S. Pat. No. 7,041,115, all of which are incorporated herein by reference. However, there always exists a need to further improve the design of the instrument while reducing the cost.

SUMMARY

One aspect of the present invention relates to a transparent cannula specifically designed for endoscopic surgical procedures. The cannula has a tubular body having a distal end and a proximate end, an open slot extending longitudinally from the beginning of the proximate end to the proximity of the distal end, and a pair of wings integrally formed on the proximate end. The tubular body is made from a transparent material and has an inner diameter large enough to accommodate an endoscope.

In one embodiment, the cannula is a slotted transparent cannula.

In another embodiment, the pair of wings are formed on opposing edges of the slot and extend radially from the tubular body.

In another embodiment, the tubular body has an inner diameter in the range of 1-10 mm, preferably 2-8 mm, and more preferably 2-5 mm.

In another embodiment, the tubular body has an outer diameter in the range of 2-12 mm, preferably 4-10 mm, and more preferably 4-7 mm.

In another embodiment, the tubular body has a length in the range of 5-25 cm, preferably 12-18 cm, and more preferably 10-15 cm.

In another embodiment, the open slot has a width in the range of 1-6 mm, preferably 1.5-5 mm, and more preferably 2-4 mm.

In another embodiment, the tubular body is made from a transparent plastic material.

In another embodiment, the transparent plastic material is selected from the group consisting of polyacrylate, polycarbonate, polystyrene, glycol modified polyethylene terephthalate, and cellulose acetate butyrate.

In another embodiment, the tubular body further comprises one or more observation holes.

Another aspect of the present invention relates to an instrument kit for implementing an endoscopic surgical procedure. The instrument kit comprises a transparent cannula guide member including a longitudinal bore having open proximal and distal ends and an open slot extending along the length thereof communicating with the open ends, and an elongate insertion member that is slidably receivable within the cannula guide member and is configured so that at least portions thereof conform with the open distal end and the open slot of the guide member to form a smooth exterior surface in combination therewith.

In one embodiment, the instrument kit further comprises an endoscope sized for insertion into the cannula guide member for direct visualization of an operative site.

In another embodiment, the endoscope is capable of carrying a cutting instrument at a leading end.

In another embodiment, the instrument kit further includes a cutting instrument mountable to the leading end of the endoscope.

In another embodiment, the instrument kit further includes a second endoscope with a cutting instrument mounted at a leading end of the second endoscope. The second endoscope is insertable into the cannula guide member such that the cutting instrument protrudes through the open slot in the cannula guide member.

In another embodiment, the instrument kit further includes a depth gauge mountable to a leading end of the endoscope.

In another embodiment, the instrument kit further includes a rasp member sized for insertion into the cannula guide member.

In another embodiment, the instrument kit further includes a locking device capable of locking the endoscope and the cannula guide member into mutually fixed positions.

In another embodiment, the instrument kit further includes a stop device mountable on the cannula guide member to prevent excessive penetration at a surgical site by the cutting instrument.

In another embodiment, the instrument kit further includes a curved dissector.

In another embodiment, the transparent cannula guide member is made from a transparent plastic material selected from the group consisting of polyacrylate, polycarbonate, polystyrene, glycol modified polyethylene terephthalate, and cellulose acetate butyrate.

Another aspect of the present invention relates to a method for implementing a uniportal endoscopic surgical procedure using the slotted transparent cannula of the present invention.

BRIEF DESCRIPTION OF THE DRAWINGS

The present invention can be better understood by reference to the following drawings. The drawings are merely exemplary to illustrate certain features that may be used singularly or in combination with other features and the present invention should not be limited to the embodiments shown.

DETAILED DESCRIPTION

Figure 1:
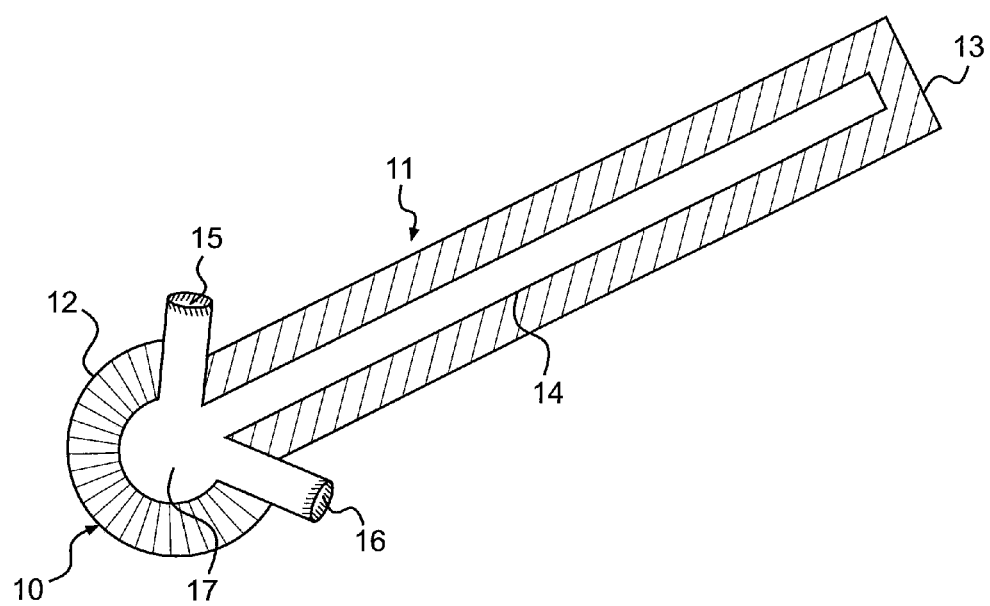
FIG. 1 illustrates a three-dimensional view of an embodiment of a slotted transparent cannula.

One aspect of the present invention relates to a slotted transparent cannula 10 (FIG. 1), specifically designed for endoscopic surgical procedures. The cannula 10 has a tubular body 11 with a proximate end 12 and a distal end 13, a slot 14 extending longitudinally from the beginning of the proximate end 12 to the proximity of the distal end 13, and a flange and a pair of wings 15 and 16 integrally formed on the proximate end 12. The slot 14 starts at the very beginning of the proximate end of the tubular body 11 so that an instrument with a matching structure, such as a protrusion, can be insert into the cannula 10 from the proximate end of the tubular body. The slot 14 ends at a short distance from the distal end of the tubular body 11 to prevent excessive advancement of cannual mount surgical tools, such as obturators or blades at the surgical site. The tubular body 11 is made from a transparent material and has an inner diameter large enough for an endoscope to pass through. In one embodiment, the wings 15 and 16 are formed on the opposing edges of the slot 14 and extend radially from the tubular body 11.

Figure 2:
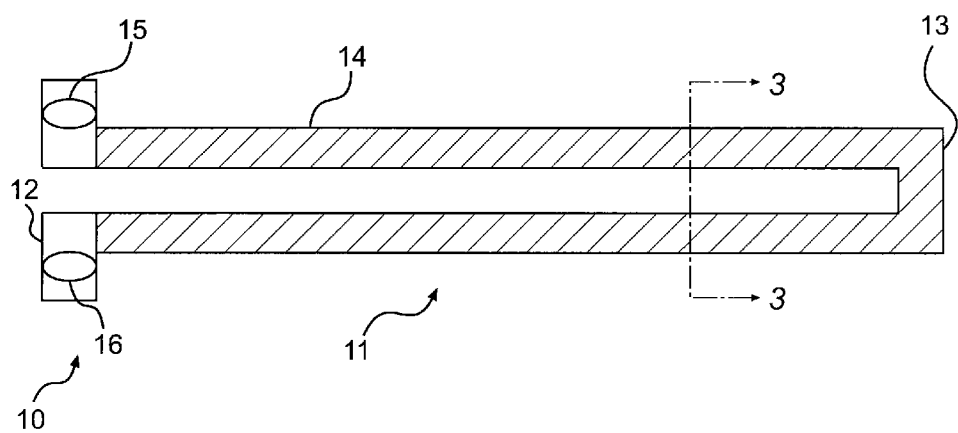
FIG. 2 illustrates a top view of the slotted transparent cannula.
Figure 3:
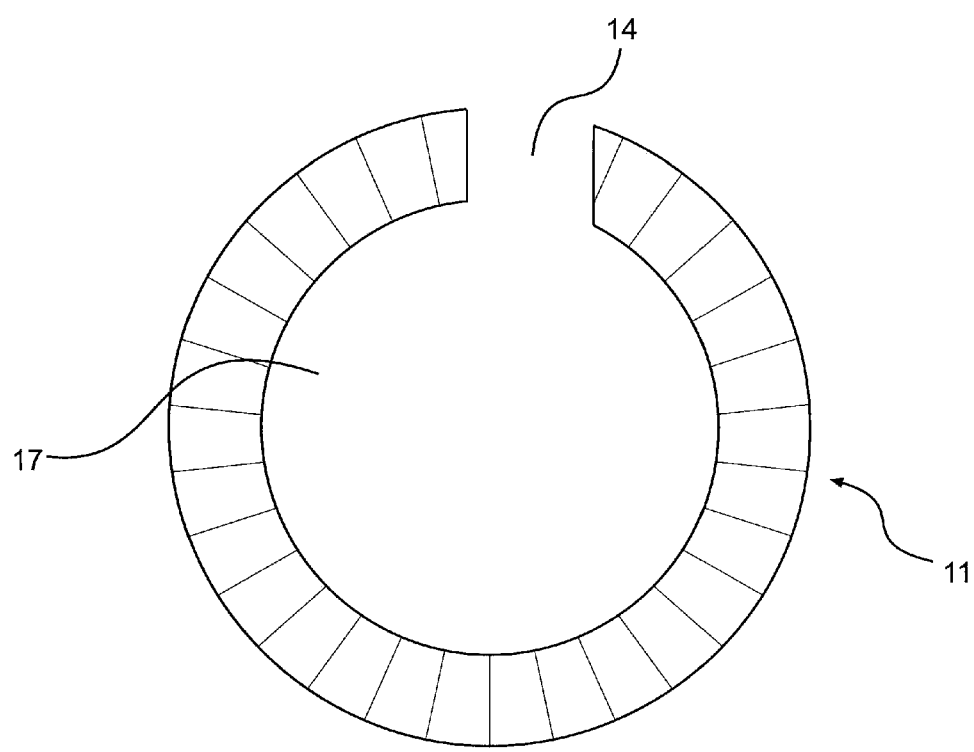
FIG. 3 illustrates a sectional view taken along line 3-3 in FIG. 2.

As shown in FIGS. 2 and 3, the tubular body 11 of the cannula 10 is circular in cross-sectional configuration and has a central aperture 17 to facilitate passage of an endoscope or other surgical devices. The central aperture 17 is sized to allow passage of the necessary surgical instruments, such as obturators and endoscopes, with sufficient clearance. In one embodiment, the central aperture has a diameter of 1-10 mm, preferably 2-8 mm, and more preferably 2-5 mm. While FIG. 2 shows a substantially circular central aperture 17, the central aperture can have a cross-section of any shape, so long as it allows the passage of an endoscope of other surgical devices. The outside diameter of the tubular body 11 varies with application but is typically in the range of 2-12 mm, preferably 4-10 mm, and more preferably 4-7 mm. The length of the tubular body 11 also varies with application. For example, the tubular body 11 would have a length of about 5-25 cm; preferably, 12-18 cm; and more preferably, 10-15 cm for carpal tunnel release and cubital tunnel release. The slot 14 allows a controlled movement of a passage of a surgical blade through the central aperture 17. In one embodiment, the slot 14 has a width in the range of 1-6 mm, preferably 1.5-5 mm, and more preferably 2-4 mm.

The wings 15 and 16 are integral parts of the tubular body 11 and extend outward radially to provide holding points for the cannula 10. In other embodiments, the wings 15 and 16 may be replaced with integrally formed outwardly extending curvilinear flange portions. In one embodiment, the flange portions are curved to match the curvature of the proximate end of an obturator. In another embodiment, the distal end of the cannula 10 may also be configured to form an integral obturator and dissector, thereby eliminating separate components.

In one embodiment, the cannula 10 is made from a transparent plastic material. As used hereinafter, the term "transparent plastic material" refers to a polymer material that has a light transmission rate equal to, or greater than, 80%. Preferably, the transparent plastic material has a light transmission rate equal to, or greater than, 90%.

Figure 17:
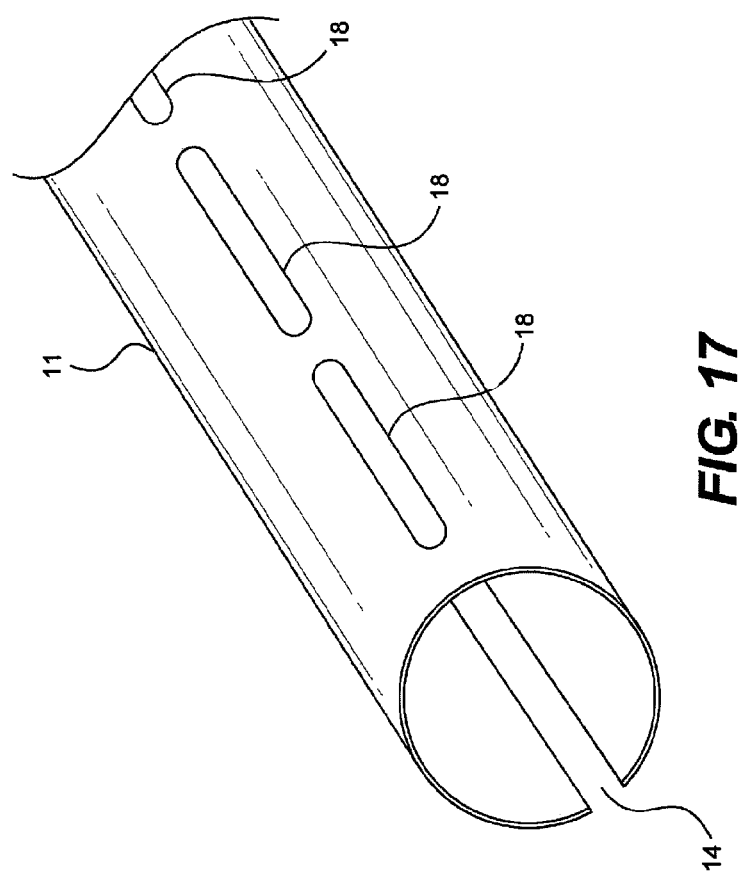
FIG. 17 illustrates observation holes in the tubular body of the cannula.

The transparency of the cannula wall makes it possible to observe the anatomical structure around the insertion path with an endoscope. In addition, the plastic cannula is lightweight and can be made by injection molding to reduce cost. The transparent plastics used in the present invention should have good impact resistance and abrasion resistance. In one embodiment, the transparent plastics may be coated with a cover layer such as alumina or diamond like carbon, to improve abrasion resistance. The tubular body may further contain observation holes 18, as exemplified in FIG. 17, for better identification of the surrounding tissue. In one embodiment, the observation holes are oblong openings on the opposite side of slot 14.

Examples of transparent plastics include, but are not limited to, polyacrylate such as polymethlamethacrylate, polycarbonate, polystyrene, glycol modified polyethylene terephthalate, and cellulose acetate butyrate. Transparent plastics are commercially available under the tradenames of Acrystex®, NAS®, Empera®, Kibiton®, Zylar®, Zytel®, etc.). The transparent cannula 10 can be used in combination with a variety of surgical instruments. Although these instruments have been shown in the Mirza U.S. Pat. Nos. 5,366,465, 5,578,051, 5,968,061 and 7,041,115, some of these instruments are described in detail herein for purposes of clarity the utility of the transparent cannula 10 of the present invention.

Figure 4:
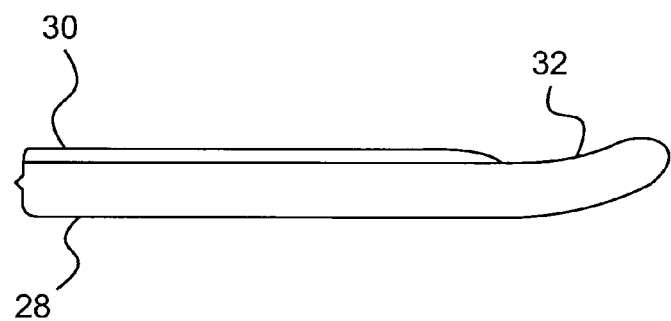
FIG. 4 illustrates a longitudinal side view of the leading end of an obturator adapted to be inserted into the slotted cannula of FIG. 1.
Figure 5:
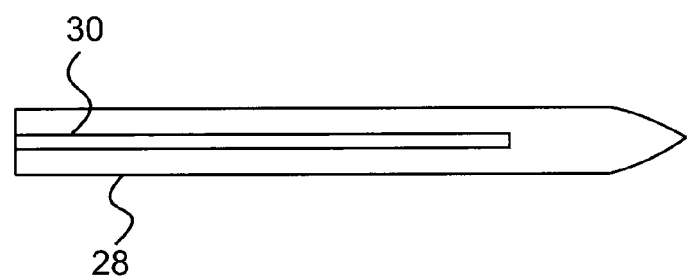
FIG. 5 illustrates a top view of the leading end of the obturator.

FIGS. 4 and 5 show an obturator 28 that is adapted to be slidably received within the cannula body 11, and presents a smooth outer surface through the intermediary of an axial, upstanding rib portion 30 which is engageable in close conformance within the longitudinal slot 14 of the cannula upon insertion therein. The distal end of the obturator 28 is a tapered tip portion 32 which is bent upwardly in a direction towards the longitudinal rib to impart to the tip a somewhat upward curvature.

Figure 6:
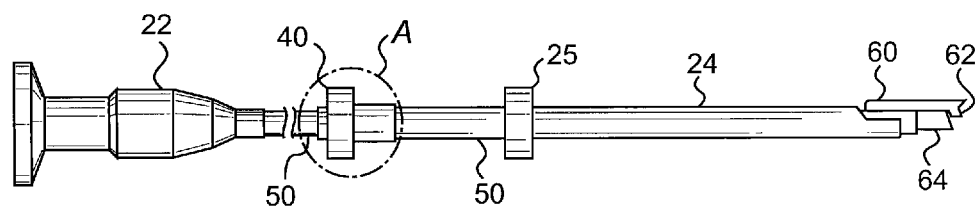
FIG. 6 illustrates a longitudinal side view of the endoscopic instrument, showing the scope and cutting device mounted on the latter inserted into the slotted cannula.
Figure 7:
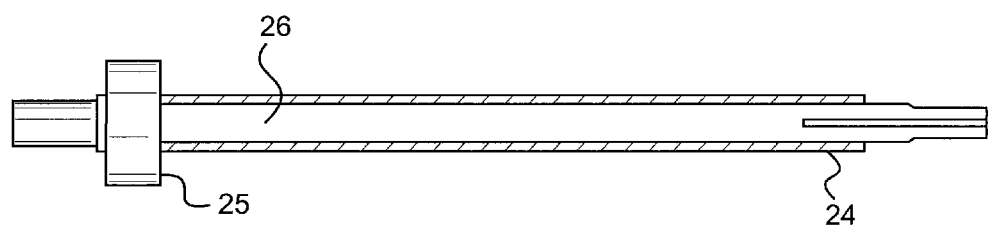
FIG. 7 illustrates a top view of the leading section of the endoscopic instrument shown in FIG. 6.
Figure 8:
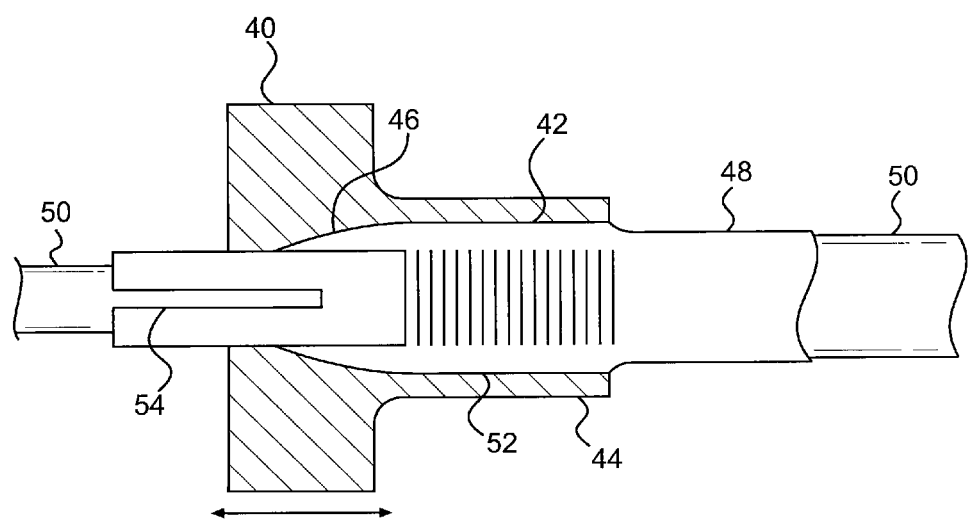
FIG. 8 illustrates, on a somewhat enlarged scale, a sectional view of the encircled portion A of the instrument of FIG. 6.
Figure 9:
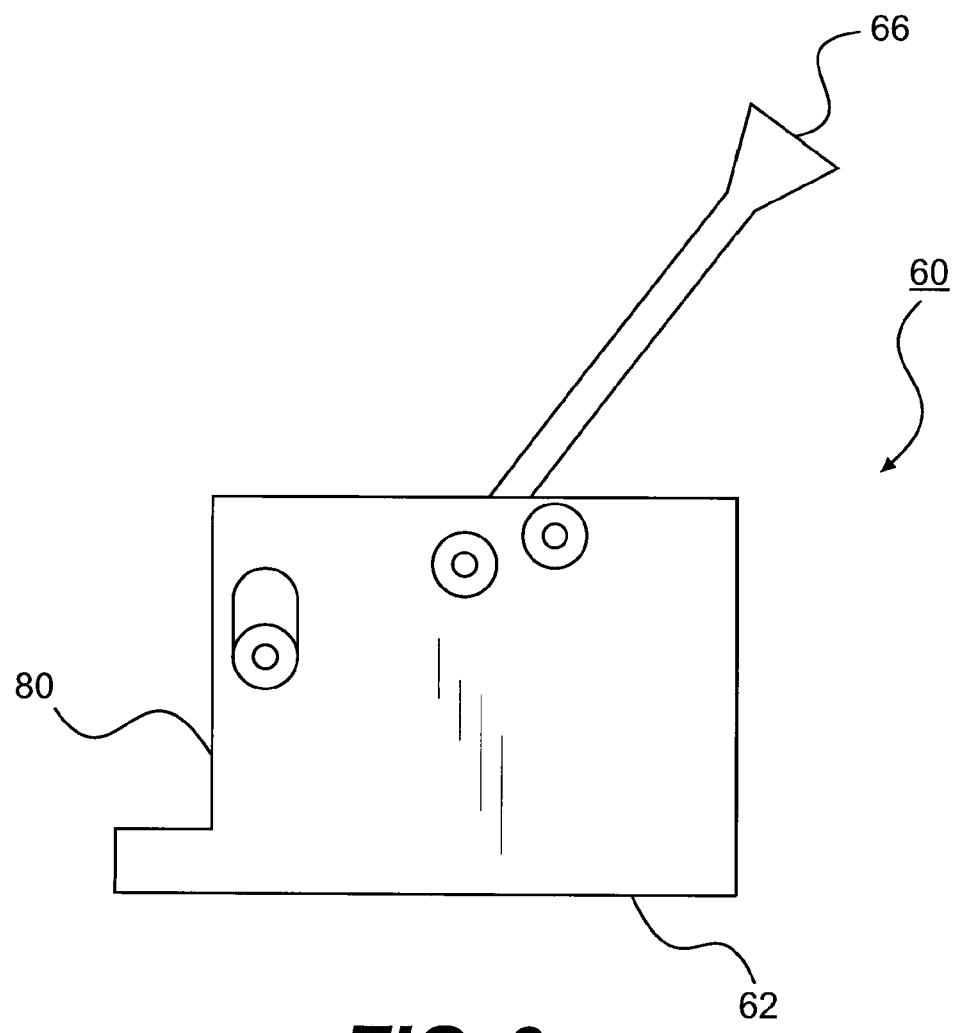
FIG. 9 illustrates a side view of the locking device.

FIGS. 6-8 show an arthroscope 22 that is adapted to be slidably received within the cannula 10. The arthroscope 22 includes a suitable knurled knob 40 having an internal threaded portion 42 in a cylindrical extension 44 and a tapered bore 46 for receiving a tubular knife or cutting blade holder 48. The blade or knife holder 48 is adapted to receive a scope 50 of cylindrical configuration extending therethrough and lock the latter within the blade holder by simply axially displacing the knurled nut 40 through threaded interengagement between the internal thread 42 of the nut and an external thread 52 on the blade holder. This will cause the tapered bore 46 of nut 40 to either compress the slotted portion 54 of the blade holder to clampingly engage the scope 50 or to loosen it so as to enable axial adjustment thereof relative to the blade holder. A regular rod-like endoscope without a blade holder may also be inserted through the cannula for effective visualization of the operative site.

FIGS. 9-12 show a locking device 60 that can be used to lock the blade holder and the transparent cannula 10 into mutually fixed positions. The locking device 60 includes a rectangular housing structure 62 with a longitudinal through bore 64 for receiving a tubular element supporting a gauge or cutting blade and for receiving a rod-like endoscope. A pivotable lever 66 mounted on the housing structure 62 is adapted to be swung between an opened position to a locked position so as to impart a clamping action to a tubular element extending through bore 64 by means of a camming structure.

Figure 10:
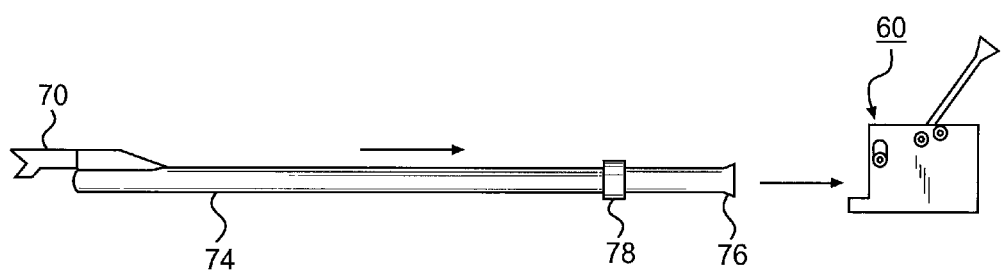
FIG. 10 illustrates a tubular member mounting a surgical knife being inserted into the locking device.

In one aspect, a cutting instrument, such as a surgical knife 70, which may be disposable, as shown in FIG. 10, is mounted at the leading end 72 of an elongate hollow tubular member 74 towards the opposite end of which the latter includes a hub portion 76 and a ring 78 spaced at a short distance therefrom, which forms a spacer defining the length of the tubular member 74 extending towards the knife blade 70, or any cutting or rasp instrument for removing tissue, such as a "curtain" of tissue, which is provided instead of the knife blade 70.

Figure 11:
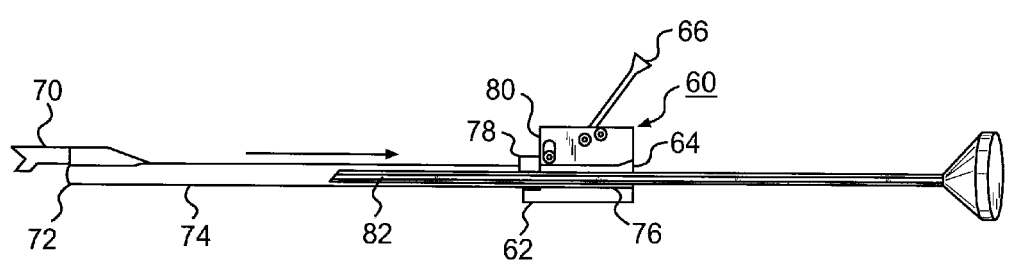
FIG. 11 illustrates the assembling of the components including an endoscope.
Figure 12:
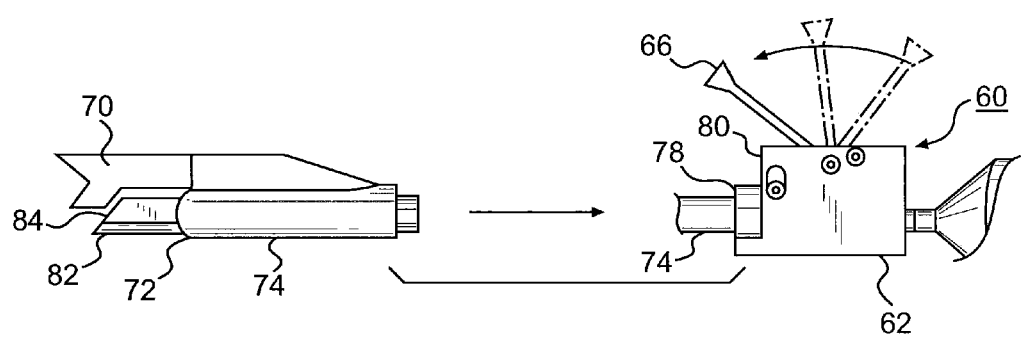
FIG. 12 also illustrates the assembling of the components including an endoscope.

As shown in FIGS. 10-12, in diagrammatic sequence, the hub end portion 76 of the hollow tubular member mounting the cutting or rasp instrument or the knife 70 at the opposite end 72 is adapted to be positioned within the bore 64 formed in the locking device 60, and is inserted therein to the extent such that the spacer 78 ring which is fastened to the tubular member 74 comes into contact with the leading or forward surface 80 of the locking device 70. At that point in time, the endoscope 82 is advanced through the hollow tubular member 74 which mounts the cutting instrument or knife 70, as shown in FIG. 11, and the leading end 84 of the endoscope 82 positioned closely to the cutting blade or instrument 70, similar to the arrangements described in the above-mentioned U.S. Pat. Nos. 5,366,465 and 5,578,051 to Mirza.

As shown in FIG. 12, as the endoscope 82 has its leading end 84 appropriately positioned in proximity relative to the knife or cutting instrument 70, the lever 66 is pivoted forwardly into the locking position, thereby causing the endoscope 82 to be clamped to the tubular member 74 mounting the cutting element or blade 70. This will then facilitate ready insertion of the resultingly locked together components into the slotted cannula 10.

Figure 13:
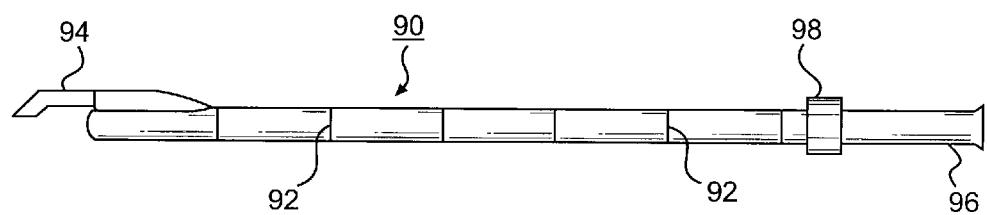
FIG. 13 illustrates the tubular member mounting a depth gauge.

The elongate tubular element 74, which mounts the knife or cutting element 70 at the leading end 72, may be calibrated along the length thereof so as to provide indication as to the depth to which the instrument is being introduced into the patient towards the surgical site. In this connection, in lieu of the tubular member mounting a knife or cutting element 70, prior to the use thereof with the endoscope 82, a tubular element 90 having calibrating markings 92 along the length thereof, which is similar to tubular element 74, may be equipped with a depth gauge 94 at the leading end thereof, as shown in FIG. 13, which, in a manner similar to the tubular member 74 mounting a knife or cutting element, is adapted to be inserted at the hub end 96 thereof into the locking device 60 until ring 98 contacts the locking device, with the endoscopic element inserted therein to provide illumination of the operating site, and the lever 66 being swung forwardly into the locking position.

Figure 14:
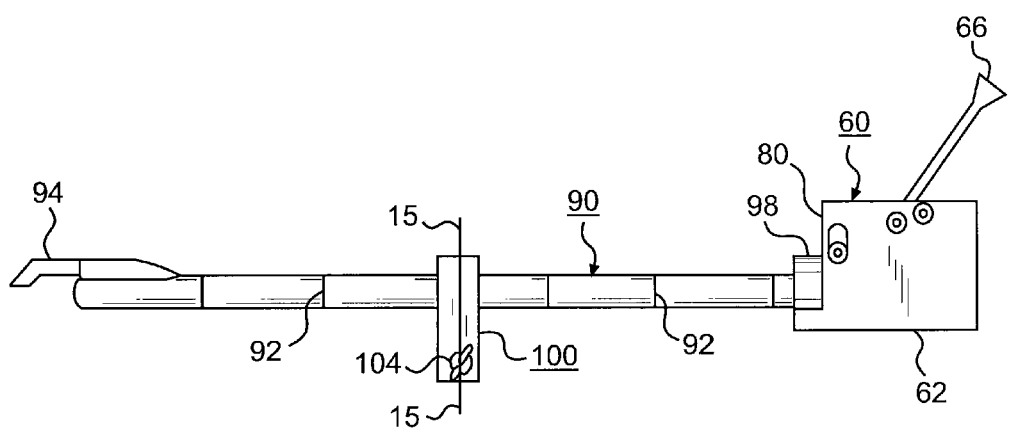
FIG. 14 illustrates the tubular member mounting the depth gauge connected to the locking device and having a stop device for limiting the extent of insertion into an incision formed in a patient.
Figure 15:
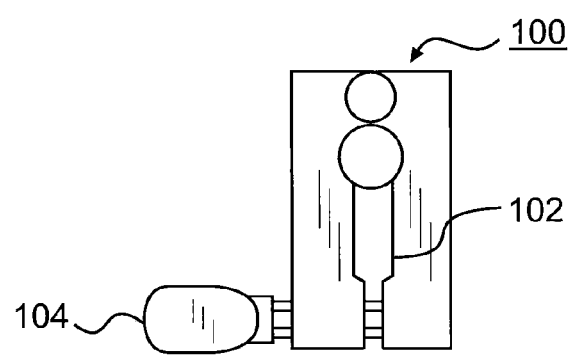
FIG. 15 is a sectional view taken along line 15-15 in FIG. 14.

Upon determination of the appropriate insertion depth to the surgical site by means of the tubular member 90 mounting the depth gauge 94, having the endoscope mounted therein, it is desirable to mount a stop device 100 in the form of a clamp member 102 on the tubular element 90 mounting the depth gauge 94, as shown in FIGS. 14 and 15, and tighten a clamping element 104, such as, for instance, a tightening screw, and which will provide information with regard to the cutting depth which is to be subsequently implemented, in that the stop device is positioned against or in proximity with the skin of the patient at the location of the incision, while the tubular element 90 and the endoscope therein are advanced within the cannula 10.

Upon withdrawing the tubular element 90 mounting the depth gauge 94 from the slotted cannula 10, a tubular element 74 mounting a knife or cutting instrument may be substituted therefore, as shown in the drawing FIGS. 10 to 12, and wherein the tubular member 74 or element mounting the knife or cutting instrument is similarly calibrated along its length. A stop device 100 is then fastened thereon at a location conforming with that of the stop device 100 which was previously mounted on the calibrated tubular member 90 mounting the depth gauge 94. This will enable the precise determination of the depth to which the cutting instrument can be inserted through the cannula 10 into the operating site, thereby preventing any injury due to any excessive penetration past the surgical site by the cutting instrument.

Figure 16:
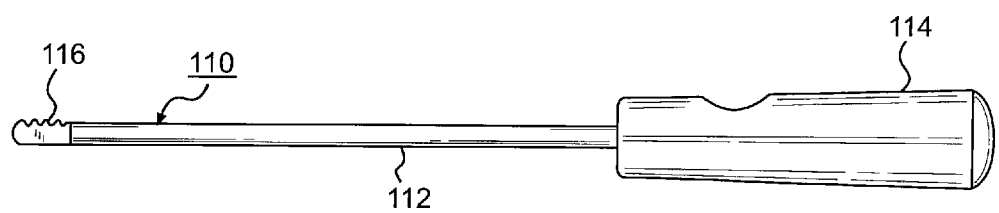
FIG. 16 illustrates a rasp member adapted to scrape a curtain of tissue at an operating site.

Furthermore, in lieu of the use of a knife blade being mounted on a tubular member 74, as the cutting element there may also be employed a unique rasp member 110 having a plurality of transverse cutting edges formed thereon, and which is adapted to scrape tissue at the operating site. The rasp member 110, as shown in FIG. 16, may be in the form of a solid rod element 112, which is insertable into the cannula 10, including a gripping end 114 and having the rasp elements 116 at the leading end thereof for advance towards the operating site. Alternatively, the rasp may comprise rasp elements mounted on a hollow tubular element similar of the type which supports the depth gauge 94 or knife 70, and is adapted to be fastened to the locking device 60 and with an endoscope passed therethrough, with the lever 66 of the locking device thereafter locking the components into mutually fixed positions.

The slotted transparent cannula and the endoscopic instruments described above may be readily applied surgical procedures such as carpal tunnel release; plantar fascia release, lateral release for patella realignment, release of the extensor tendons for lateral epicondylitis (tennis elbow), release of the posterior and other compartments of the leg, and forearm fascia release for fascial compartment syndrome. It is also possible to customize the slotted transparent cannula to adapt to other endoscopic surgical instrument for other endoscopic surgical procedures.

Another aspect of the present invention relates to an instrument kit for implementing an endoscopic surgical procedure. The instrument kit contains a transparent cannula guide member including a longitudinal bore having open proximal and distal ends and an open slot extending along the length thereof communicating with the open ends, and an elongate insertion member that is slidably receivable within the cannula guide member and is configured so that at least portions thereof conform with the open distal end and the open slot of the guide member to form a smooth exterior surface in combination therewith.

In one embodiment, the instrument kit further includes an endoscope sized for insertion into the cannula guide member for direct visualization of an operative site.

In another embodiment, the endoscope is capable to carry a cutting instrument at a leading end.

In another embodiment, the instrument kit further includes a cutting instrument mountable to the leading end of the endoscope.

In another embodiment, the instrument kit further includes a second endoscope with a cutting instrument mounted at a leading end of the second endoscope. The second endoscope is insertable into the cannula guide member such that the cutting instrument protrudes through the open slot in the cannula guide member.

In another embodiment, the instrument kit further includes a depth gauge mountable to a leading end of the endoscope.

In another embodiment, the instrument kit further includes a rasp member sized for insertion into the cannula guide member.

In another embodiment, the instrument kit further includes a locking device capable of locking the endoscope and the cannula guide member into mutually fixed positions.

In another embodiment, the instrument kit further includes a stop device mountable on the cannula guide member to prevent excessive penetration at a surgical site by the cutting instrument.

In another embodiment, the instrument kit further includes a curved dissector.

Another aspect of the present invention relates to a method for implementing a uniportal endoscopic surgical procedure using the slotted transparent cannula of the present invention. In one embodiment, the method includes the steps of making an incision on a patient in need of such endoscopic surgical procedure at a location proximate an operation site to establish an entry portal, inserting an elongate insertion member into a longitudinal bore of an elongate transparent cannula having open proximal and distal ends and an open slot extending along the length of the transparent cannula, the elongate insertion member being configured to form a smooth exterior surface at the open distal end of the transparent cannula when fully inserted into the transparent cannula; introducing the distal end of the transparent cannula/insertion member combination into the entry portal and advancing the combination a predetermined distance relative to the operation site; withdrawing the insertion member while permitting the transparent cannula to remain in place at the operation site; inserting a first endoscope into the transparent cannula for direct visualization of anatomic structures surrounding the transparent cannula and positioning of the transparent cannula at the operative site; withdrawing the first endoscope from the transparent cannula; mounting a cutting instrument on a leading end of a second endoscope; inserting the second endoscope with the cutting instrument into the transparent cannula such that the cutting instrument protrudes into the open slot in the transparent cannula, and advancing the second endoscope so that the cutting instrument is in contact with a target tissue at the operation site; operatively engaging the target tissue with the cutting instrument while advancing the latter under direct visualization through the second endoscope so as to perform a desired operative procedure on the target tissue; withdrawing the second endoscope and the cutting instrument from the transparent cannula; withdrawing the transparent cannula through the entry portal; and suturing the incision.

In one embodiment, the first endoscope and the second endoscope are the same endoscope. In another embodiment, the first endoscope and the second endoscope are different endoscopes.

The transparent cannula of the present invention can be inserted into the tissue through a small opening and advanced to a surgical site, thus forming a passageway towards the surgical site. The passageway allows the insertion of the endoscope and other instruments to the surgical site without further damages to the surrounding tissues. The transparent cannula body also allows endoscopic examination of the surrounding anatomical structures without any movement of the cannula body. The longitudinal slot provides improved visualization of the target anatomical structure and control over the inserted devices. The cannula is lightweight and can be produced at low cost. The slotted transparent cannula can be used in endoscopic surgical procedures such as carpal tunnel release, cubital tunnel release, plantar fascia release, lateral release for patella realignment, release of the extensor tendons for lateral epicondylitis (tennis elbow), release of the posterior and other compartments of the leg, and the forearm fascial release for fascial compartment syndrome.

The present invention is further illustrated by the following examples which should not be construed as limiting. The contents of all references, patents and published patent applications cited throughout this application, as well as the Figures and Tables are incorporated herein by reference.

Example 1

Use of the Slotted Transparent Cannula (Hereinafter "Clear Cannula") For Endoscopic Carpal Tunnel Release 1-a. Preparation of the Clear Cannula Prepare the Clear Cannula for insertion by introducing the obturator through the cannula. The prong at the distal end of the obturator should be between the wings of the cannula. This ensures that the distal tip of the obturator is oriented correctly.

1-b. Introduction of Clear Cannula:

A single incision is made in the palm proximate the distal side of the transverse carpal ligament (TCL). A curved dissector is inserted to form a passage beneath the TCL. Once the pathway is created and the dissector removed, the obturator and the Clear Cannula are introduced into the same pathway. The cannula tip should always stay against the under surface of the TCL and superficial to the flexor tendons and ulnar bursa. Prior to removal of the obturator rotate the assembly so the slot of the cannula faces slightly toward the ulnar side. The cannula should not be rotated past two and ten o'clock respectively.

1-c. Endoscopic Visualization of Anatomy:

A 4 mm, 30 degree endoscope, oriented towards the slot of the cannula, is then introduced into the cannula. Visualization of the transverse carpal ligament fibers and fibers of the antebrachial fascia should be visible through the slotted portion of the cannula. If the transverse fibers of the TCL are not clearly seen, the cannula must be removed using the obturator and the introduction procedure repeated.

The Clear Cannula should allow for adequate visualization of the median nerve and flexor tendons without the need to rotate the slot of the cannula towards these anatomic structures. Due to variations of anatomy, visual confirmation of these structures may not be possible. If visualization of these structures is inadequate, the surgeon may rotate the slot of the cannula towards the median nerve (radial) and flexor tendons (ulnar) to verify proper cannula placement.

1-d. Division of the Transverse Carpal Ligament:

With a clear view of the transverse fibers of the TCL and no other intervening structures visible within the slotted portion of the cannula, the endoscope is removed from the cannula. The scope-mounting blade is attached to the endoscope via the locking device.

The scope-mounting blade/scope assembly is introduced into the cannula and, as the surgeon observes the monitor, the TCL is divided by advancing the scope-mounted blade through the cannula in a proximal direction.

Once division is complete, remove the blade/scope assembly from the cannula, remove the blade from the endoscope and confirm division by reintroducing the endoscope into the cannula. Once division has been verified remove the Clear Cannula by reintroducing the obturator. The Clear Cannula should not be removed without first introducing the obturator).

This procedure dramatically reduces the risk of damaging any tissue and nerves, such as the median nerve, in the vicinity of the operating site. It also enables the surgeon to exercise an improved degree of control over the possibly single-handed manipulation of the endoscopic instrument and cutting blade.

Example 2

Use of the Clear Cannula for Endoscopic Cubital Tunnel Release 2-a. Preparation of the Clear Cannula Prepare the Clear Cannula for insertion by introducing the obturator through the cannula. The prong at the distal end of the obturator should be between the wings of the cannula. This ensures that the distal tip of the obturator is oriented correctly.

2-b. Introduction of the Clear Cannula:

An "X" I splaced on both the medial epicondyle and olecrnon. A 3-4 cm incision is made along the course of the ulnar nerve at the cubital tunnel between the marked anatomical structures. A dissector is inserted to form a passage beneath the distal and proximal ulnar sheath. Once the distal or proximal pathway is created and the dissector removed, introduce the obturator and Clear Cannula into the same pathway. The surgeon should have direct visualization of the ulnar nerve so that the slotted portion of the cannula can be positioned 180 degrees to the ulnar nerve. Remove the obturator.

2-c. Endoscopic Visualization of Anatomy:

A 4 mm, 30 degree endoscope, oriented towards the slot of the cannula, is then introduced into the cannula. Visualization of the (distal/proximal) ulnar nerve sheath should be visible through the slotted portion of the cannula. If the transverse fibers of the fascia are not clearly seen, the cannula must be removed using the obturator and the introduction procedure repeated.

The Clear Cannula should allow for adequate visualization of the ulnar nerve and surrounding tissue without the need to rotate the slot of the cannula towards these anatomic structures. Due to variations of anatomy, visual confirmation of the ulnar nerve may not be possible. If visualization is inadequate, the surgeon may rotate the slot of the cannula towards the ulnar nerve to verify proper cannula placement.

2-d. Division of the Distal and Proximal Ulnar Sheath:

With a clear view of the transverse fibers of distal/proximal ulnar sheath and no other intervening structures visible within the slotted portion of the cannula, the endoscope is removed from the cannula. The scope-mounting blade is attached to the endoscope via the locking device.

The scope-mounting blade/scope assembly is introduced into the cannula and, as the surgeon observes the monitor, the sheath is divided by advancing the scope-mounted blade through the cannula.

Once division is complete, remove the blade/scope assembly from the cannula, remove the blade from the endoscope and confirm division by reintroducing the endoscope into the cannula. Once division has been verified, remove the Clear Cannula by reintroducing the obturator. The Clear Cannula should not be removed without first introducing the obturator.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A slotted cannula for endoscopic surgical procedures, comprising: a tubular body comprising: a distal end; a proximate end; an outer surface; an open slot extending longitudinally from the beginning of the proximate end to the proximity of the distal end; and a pair of substantially cylindrical, non-flexible wings integrally formed on the proximate end, on opposing edges of the slot and separately protruding outward from the outer surface of the tubular body radially along different axes that pass through the longitudinal centerline of the cannula and at an angle to one another and wherein no longitudinal plane through the centerline of the cannula passes through both wings, wherein the tubular body is made from a transparent polymer material and has an inner diameter that accommodates an endoscope, wherein the transparent polymer material allows the observation of anatomical structure around an insertion path of the cannula.

2. The slotted cannula of claim 1, wherein the tubular body has an inner diameter in the range about 140 mm.

3. The slotted cannula of claim 2, wherein the tubular body has an inner diameter in the range about 2-8 mm.

4. The slotted cannula of claim 3, wherein the tubular body has an inner diameter in the range about 2-5 mm.

5. The slotted cannula of claim 1, wherein the tubular body has an outer diameter in the range about 2-12 mm.

6. The slotted cannula of claim 5, wherein the tubular body has an outer diameter in the range about 4-10 mm.

7. The slotted cannula of claim 5, wherein the tubular body has an outer diameter in the range about 4-7 mm.

8. The slotted cannula of claim 1, wherein the tubular body has a length in the range about 5-25 cm.

9. The slotted cannula of claim 8, wherein the tubular body has a length in the range about 12-18 cm.

10. The slotted cannula of claim 9, wherein the tubular body has a length in the range about 10-15 cm.

11. The slotted cannula of claim 1, wherein the slot has a width in the range about 1-6 mm.

12. The slotted cannula of claim 11, wherein the slot has a width in the range about 2-4 mm.

13. The slotted cannula of claim 1, wherein the tubular body is made from a transparent plastic material.

14. The slotted cannula of claim 13, wherein the transparent plastic material is selected from the group consisting of polyacrylate, polycarbonate, polystyrene, glycol modified polyethylene terephthalate, and cellulose acetate butyrate.

15. The slotted cannula of claim 14, wherein the transparent plastic material has a light transmission rate equal to or greater than 80%.

16. The slotted cannula of claim 1, wherein the tubular body further comprises one or more observation holes.

17. An instrument kit for implementing an endoscopic surgical procedure, said instrument kit comprising; a slotted cannula for endoscopic surgical procedures, comprising: a tubular body comprising: a distal end; a proximate end; an outer surface; an open slot extending longitudinally from the beginning of the proximate end to the proximity of the distal end; and a pair of substantially cylindrical, non-flexible wings integrally formed on the proximate end, on opposing edges of the slot and separately protruding outward from the outer surface of the tubular body radially along different axes that pass through the longitudinal centerline of the cannula and at an angle to one another and wherein no longitudinal plane through the centerline of the cannula passes through both wings, wherein the tubular body is made from a transparent polymer material and has an inner diameter that accommodates an endoscope, wherein the transparent polymer material allows the observation of anatomical structure around an insertion path of the cannula; and an elongate insertion member being slidably receivable within said cannula guide member and being configured so that at least portions thereof conform with said open distal end and said open slot of the guide member to form a smooth exterior surface in combination therewith.

18. The instrument kit of claim 17, further comprising an endoscope sized for insertion into said slotted cannula for direct visualization of an operative site.

19. The instrument kit of claim 18, wherein the endoscope is capable to carry a cutting instrument at a leading end.

20. The instrument kit of claim 19, further comprising a cutting instrument mountable to the leading end of the endoscope.

21. The instrument kit of claim 18, further comprising:
a second endoscope with a cutting instrument mounted at a leading end of said second endoscope,
wherein the second endoscope is insertable into the slotted cannula such that the cutting instrument protrudes through the open slot in the cannula.

22. The instrument kit of claim 18, further comprising a depth gauge mountable to a leading end of the endoscope.

23. The instrument kit of claim 18, further comprising a rasp member sized for insertion into the slotted cannula.

24. The instrument kit of claim 18, further comprising a locking device capable of locking the endoscope and the slotted cannula into mutually fixed positions.

25. The instrument kit of claim 24, further comprising a stop device mountable on the slotted cannula to prevent excessive penetration at a surgical site by the cutting instrument.

26. The instrument kit of claim 17, further comprising a curved dissector.

27. The instrument kit of claim 17, wherein the slotted cannula comprises a transparent plastic material selected from the group consisting of polyacrylate, polycarbonate, polystyrene, glycol modified polyethylene terephthalate, and cellulose acetate butyrate.

28. A method for implementing a uniportal endoscopic surgical procedure, comprising: a) making an incision on a patient in need of such endoscopic surgical procedure at a location proximate an operation site to establish an entry portal; b) inserting an elongate insertion member into slotted cannula for endoscopic surgical procedures, said slotted cannula comprising: a tubular body comprising: a distal end; a proximate end; an outer surface; an open slot extending longitudinally from the beginning of the proximate end to the proximity of the distal end; and a pair of substantially cylindrical, non-flexible wings integrally formed on the proximate end, on opposing edges of the slot and separately protruding outward from the outer surface of the tubular body radially along different axes that pass through the longitudinal centerline of the cannula and at an angle to one another and wherein no longitudinal plane through the centerline of the cannula passes through both wings, wherein the tubular body is made from a transparent polymer material and has an inner diameter that accommodates an endoscope, wherein the transparent polymer material allows the observation of anatomical structure around an insertion path of the cannula, the elongate insertion member being configured to form a smooth exterior surface at the open distal end of the cannula when fully inserted into the cannula; c) introducing the distal end of the cannula/insertion member combination into the entry portal and advancing the combination a predetermined distance relative to the operation site; d) withdrawing the insertion member while permitting the cannula to remain in place at the operation site; e) inserting a first endoscope into the cannula for direct visualization of anatomic structures surrounding the cannula and positioning of the cannula at the operative site; f) withdrawing the first endoscope from the cannula; g) inserting the second endoscope with the cutting instrument into the cannula such that the cutting instrument protrudes into the open slot in the cannula; h) advancing the second endoscope so that the cutting instrument is in contact with a target tissue at the operation site; i) operatively engaging the target tissue with the cutting instrument while advancing the latter under direct visualization through the second endoscope so as to perform a desired operative procedure on the target tissue; j) withdrawing the second endoscope and the cutting instrument from the cannula; and k) withdrawing the cannula through the entry portal.

29. The method of claim 28, further comprises the step of mounting a cutting instrument on a leading end of a second endoscope after said step of withdrawing the first endoscope from the cannula.

30. The method of claim 28, wherein the first endoscope and the second endoscope are the same endoscope.

31. The method of claim 28, wherein the first endoscope and the second endoscope are different endoscopes.

* * * * *